United States Patent
Nath et al.

(10) Patent No.: US 6,199,431 B1
(45) Date of Patent: *Mar. 13, 2001

(54) METHOD OF RESONANT LIFE CYCLE COMPARISON INSPECTION BY SERIAL NUMBER

(75) Inventors: Robert H Nath; James J Schwarz, both of Albuquerque; Jay G Saxon, Corrales, all of NM (US)

(73) Assignee: Quasar International, Inc., Albuquerque, NM (US)

(*) Notice: Subject to any disclaimer, the term of this patent is extended or adjusted under 35 U.S.C. 154(b) by 0 days.

This patent is subject to a terminal disclaimer.

(21) Appl. No.: 09/266,845

(22) Filed: Mar. 12, 1999

Related U.S. Application Data

(63) Continuation-in-part of application No. 08/826,149, filed on Mar. 27, 1997, now Pat. No. 5,886,263.

(51) Int. Cl.$^7$ .............................. G01N 29/12; G06G 7/68
(52) U.S. Cl. .................. 73/579; 73/587; 73/602; 700/30; 700/31; 702/36
(58) Field of Search ............................. 73/579, 602, 587, 73/594, 592, 659, 660; 700/31, 30; 702/36

(56) References Cited

U.S. PATENT DOCUMENTS

| | | | |
|---|---|---|---|
| 4,799,387 | 1/1989 | Matsuo | 73/620 |
| 4,976,148 | 12/1990 | Migliori et al. | 73/579 |
| 4,984,173 | * 1/1991 | Imam et al. | 700/279 |
| 5,062,296 | 11/1991 | Migliori | 73/579 |
| 5,327,358 | * 7/1994 | Stubbs | 702/36 |
| 5,351,543 | 10/1994 | Migliori et al. | 73/579 |
| 5,355,731 | 10/1994 | Dixon et al. | 73/579 |
| 5,408,880 | 4/1995 | Rhodes et al. | 73/579 |
| 5,425,272 | 6/1995 | Rhodes et al. | 73/579 |
| 5,493,511 | * 2/1996 | Wincheski et al. | 702/39 |
| 5,495,763 | 3/1996 | Rhodes et al. | 73/579 |
| 5,533,399 | * 7/1996 | Gibson et al. | 73/579 |
| 5,686,667 | * 11/1997 | McCollum et al. | 702/76 |
| 5,886,263 | * 3/1999 | Nath et al. | 73/579 |

* cited by examiner

Primary Examiner—Hezron Williams
Assistant Examiner—Jacques Saint-Surin
(74) Attorney, Agent, or Firm—Ronald R. Snider; Snider & Associates

(57) ABSTRACT

Modal frequencies of known good sample parts (SN) are analyzed to determine a pattern which will identify acceptable material and dimensional variations. The data obtained by analysis is then archived. Production parts are then measured at the modal frequencies and the production parts are accepted or rejected after pattern analysis of each part by comparing the production part with response to the pattern identified as acceptable for material and dimensional variations. Production part data is archived for future testing. This procedure is repeated throughout the lifetime of a part, and may be used on parts which are part of an assembly, including other unmeasured parts.

7 Claims, 2 Drawing Sheets

METHOD OF RESONANT LIFE CYCLE COMPARISON INSPECTION BY SERIAL NUMBER

This application is a continuation in part of U.S. patent application Ser. No. 08/826,149 now U.S. Pat. No. 5,886,263 filed on Mar. 27, 1997.

BACKGROUND OF THE INVENTION

1. Field of the Invention

This invention relates to the field of resonant ultrasound spectroscopy (RUS) and more particularly to the use of the data generated by RUS for developing testing criteria and pattern analysis; testing of production parts using pattern analysis; and use during maintenance procedures of archival resonant frequency records and pattern analysis for subsequent comparison testing of each individual part compared to its unique archived previous measurements, as identified by serial number.

2. The Prior Art

Resonant ultrasound testing is known in the prior art as exemplified by U.S. Pat. No. 4,976,148 Migliori et al., U.S. Pat. No. 5,062,296 Migliori et al., U.S. Pat. No. 5,351,543 Migliori et al. U.S. Pat. No. 5,355,731 Dixon et al., U.S. Pat. No. 5,495,763 Rhodes et al., U.S. Pat. No. 5,408,880 Rhodes et al., and U.S. Pat. No. 5,425,272 Rhodes et al., plus recent issued cases, all of which are incorporated therein by reference.

U.S. Pat. No. 5,355,731 teaches measurement of sphericity utilizing resonant ultrasound spectroscopy. In this disclosure, a first set of calculations are used to determine resonant frequencies as the functions of Poisson's ratio where the spherical objects have an ideal dimension. Next, calculations are made to determine a set of resonant frequencies where there is a deviation from dimensions of the ideal object dimensions. Then a production object is measured by resonant ultrasound (RUS), and is compared to the calculated values to determine the deviation from the ideal object dimensions.

Migliori U.S. Pat. No. 4,976,148 teaches the use of resonant ultrasound spectroscopy (RUS) for determination of elastic constants of a sample.

BRIEF SUMMARY OF THE INVENTION

The prior art includes strain gauge devices embedded in parts which can indicate deformation when compared to historical baseline data. This can indicate that the metal has been deformed or yielded. It can also measure a strain, and if measurements are made while the structure is being stressed in a precise quantitative manner, it will permit the inference of a change in elastic modulus due to fatigue, overload, heat damage, or some other factor. In other words, connecting a resistance measurement instrument to an aircraft landing gear with a built-in strain gauge will tell only if the metal has already yielded, i.e., permanently stretched. This is considered to be a metal failure unless there is a known load change placed upon the assembly causing the strain.

In this invention, Applicant provides for a complete method of resonant inspection for periodic maintenance which encompasses the entire life of a product or component. Applicant initially provides for measurement of resonant mode frequencies of a prototype to obtain empirical data, measurement of resonant mode frequencies of at least one production part upon completion of manufacture of a production part, pattern analysis of those resonant mode frequencies, comparison of resonant mode frequencies of at least one production part to the prototype resonant mode frequencies to obtain comparative data, and subsequent inspecting of at least one production part at maintenance intervals by comparing its resonant mode frequencies and a pattern analysis of these frequencies to resonant mode frequencies and pattern analysis data recorded in memory at the time the part was produced. The inspection measurements and pattern analysis results are added to the archived record for that serial number part, at each inspection interval. Archived records can then be compared to subsequent inspection measurement results to establish a history of part changes or deterioration.

This invention is particularly advantageous for use in testing components of high value and significant consequences in the event of a failure, such as aircraft turbine rotors and disks. Testing is upon initial manufacture, and for subsequent periodic maintenance. The use of resonant ultrasound spectroscopy (RUS) measurements with this method permits detection of flaws which develop within periodic maintenance intervals, or as they develop in the components during the intervening periods of operation. It is possible to detect stress failures and metal structure precursors to cracks in parts which may occur internally even prior to the development of internal or external cracks. This technique, therefore, leads to detection of potentially catastrophic failures in aircraft landing gear, aircraft rotors and disks long before such failure may occur, and before it can be detected by other non-destructive means. This method also provides an archived record of objective measurements and pattern analysis results relating to the structural integrity of each component at the time of the inspection.

DETAILED DESCRIPTION

Figure 1:
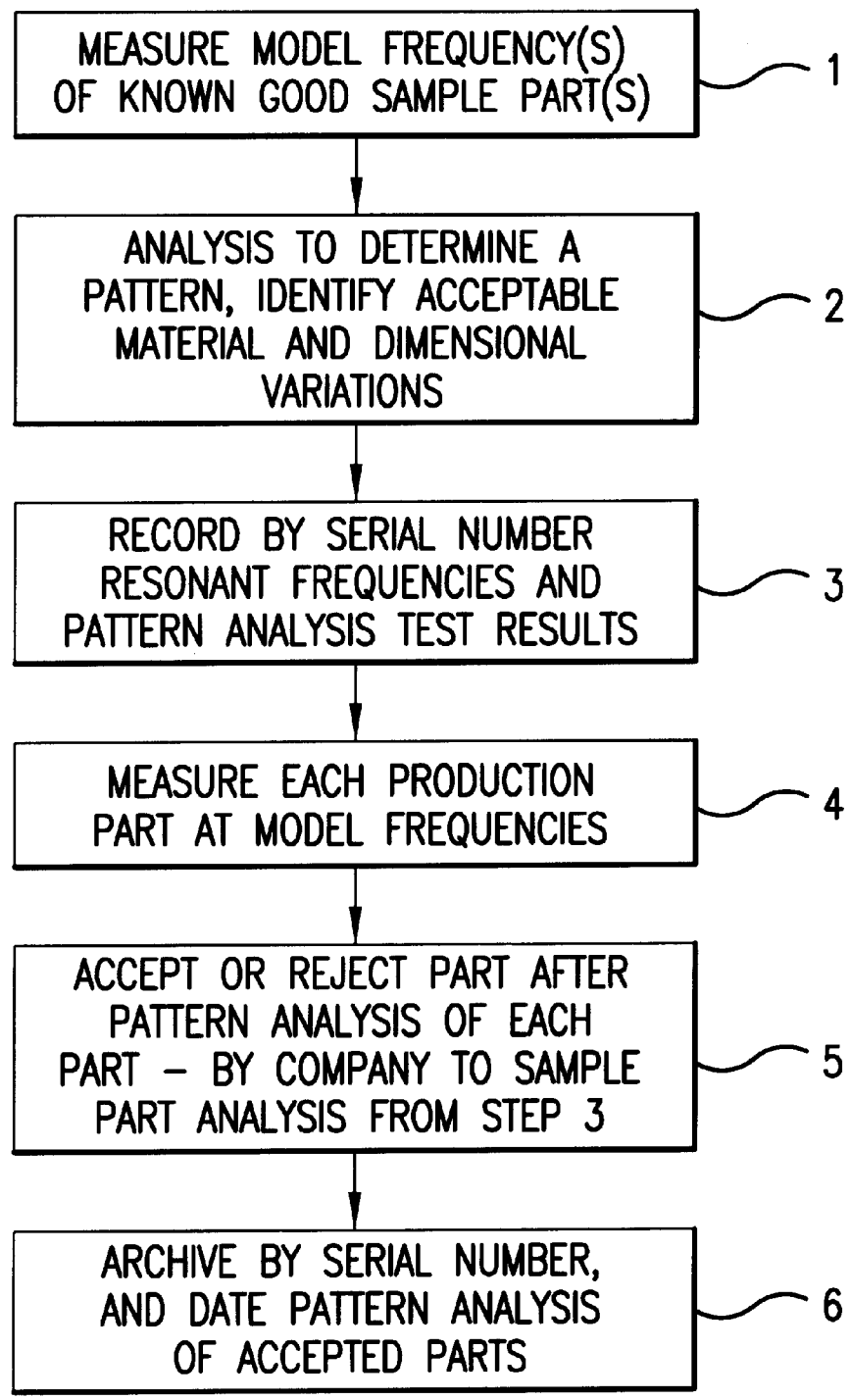
FIG. 1 shows a block diagram of the steps of the method of this invention.

FIG. 1 shows in block form the steps of this invention. This testing may occur at ambient temperatures and/or at temperatures for which it is anticipated that the part will operate.

As shown in Block 1, the first step is the measurement of the multiple resonant modal frequencies of one or more sample parts to obtain empirical data for this type of part. obviously, this part (or these parts) should be one which has been verified to be accurate, both in dimensions and material properties, with no defects. These must be known good parts.

As shown in Block 2, resonant mode frequency patterns are then analyzed to determine a pattern to identify the acceptable material and dimensional variations. As shown in Block 3, resonant mode frequencies and pattern analysis test results are recorded and archived by serial number for future reference comparison. As shown in Block 4, measurement of the same resonant mode frequencies are taken for each production part when new at the point of manufacture and analyzed to confirm the structural characteristics of the new part.

In Block 5, there is shown a step wherein the part is accepted for further part non-destructive testing or rejected for structural failure to pass inspection based on the pattern analysis criteria that identify the deviations from acceptable structural variations that are found in "acceptable" parts.

Figure 2:
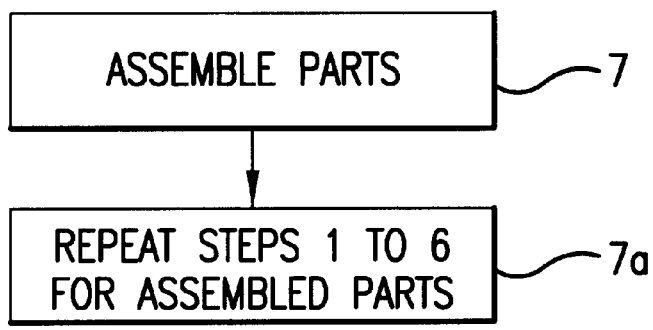
FIG. 2 shows a block diagram of a procedure for testing assemblies.

In Block 6 of FIG. 2, the peak frequencies and pattern analysis results are archived by serial number.

In Block 7, there is shown an additional step needed for those operations that perform preassembly tests such as turbine wheel spin tests. This step could also or alternatively consist of an in-situ assembled RUS measurement.

In Block 8 (FIG. 3), there is shown the after manufacture periodic inspection of the part wherein inspection or overhaul includes resonant measurement and analysis. This can be in situ or disassembled.

Figure 3:
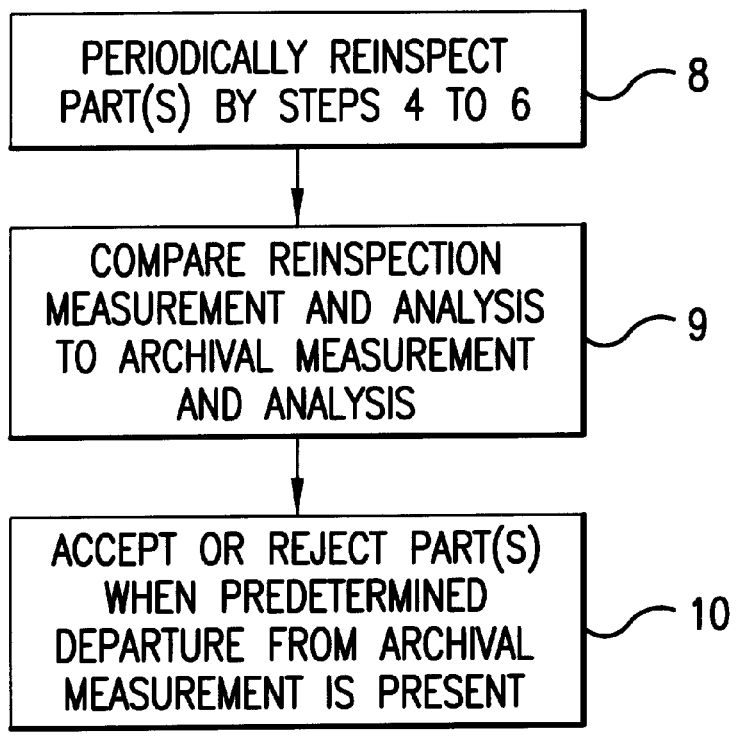
FIG. 3 shows a block diagram for periodic reinspection.

In FIG. 3, Block 8, the steps of blocks 4 to 6 are performed and analysis results are recorded and archived (Block 6).

In Block 9, the most recent resonant inspection (measurement and analysis) results are compared to the archival resonant frequency measurement and analysis data. This is based upon the original part inspection at the factory, and any interim maintenance inspection data.

The resonant maintenance comparison in Block 9 will signal any significant change in a part such as a turbine rotor. These changes can include cracks or growth of small internal material flaws, heat-caused changes in material either general or localized, fatigue-induced changes in material even before cracks appear, and impact damaged area if the damage causes local anisotropy not present in the rotor when the rotor baseline was first measured upon manufacture. Block 10, FIG. 3, shows a final step of accepting or rejecting parts which have been in service after the comparison step shows a predetermined departure from archival data.

All recording and archiving of peak frequencies and pattern analysis results by serial number.

Blocks 8, 9 and 10 of FIG. 3 are repeated at every periodic scheduled resonant inspection for the life of the part.

The archival resonant frequency data can also be analyzed to determine trends in part performance, i.e., gradual degradation of the part over a period of time. An example of this degradation is the reduction of the desirable residual compressive stress on the surface of turbine discs and on bearing race surfaces.

The use of resonant testing and verification based upon known good parts allows better process control in production, more complete manufacturing inspection and provides improved component life quality assurance because of the measurements of structural integrity, at each overhaul, thus permitting the prolonged use of safety critical components.

Permanent Attachment of Transducers

In part manufacture, archival data recording, and subsequent maintenance testing, it may be desirable to utilize piezoelectric crystals (with backloading) which are permanently attached to parts which are undergoing periodic maintenance inspection. The use of permanently attached piezoelectric crystals provides for repeat measurement at exactly the same location under the same conditions, and hence eliminates any variables that may be associated with crystal attachment or measurement location on the part. Still further, permanent crystal attachment allows measurement at part locations which may not be readily accessible once a part is installed in a larger assembly such as an aircraft.

A part structure, with a small permanently attached piezoelectric crystal, can be mechanically excited through a sweep of frequencies by a portable vibration source controlled by test instruments as described above. The piezoelectric crystals with backloads weigh only a few ounces per one hundred and the material costs for such crystals is only in the order of $20.00 per hundred. Resonant frequency measurements with this type of crystal are generally in excess of 1 Kh.

Because this type of permanently attached piezoelectric crystal can be added after an aircraft is built, it can be applied to many of the aircraft parts. Still further, the after-built feature allows retrofitting on current commercial and military fleets. For new aircraft, there is also no need to requalify existing materials for aircraft construction to allow for unknown effects of the internal incorporation of foreign objects such as sensors. If the material already has embedded into it or attached to it, piezoelectric sensors and actuators, these are taken into consideration in all subsequent measurements.

In critical aircraft parts such as those in landing gear assemblies, up to 100 safety critical locations may be selected and 100 permanently attached piezoelectric crystals can be attached thereto which will permit a verification of the unchanged condition of the assembled and thus constrained components of a landing gear assembly when compared to baseline resonance patterns recorded and archived at a time that the assembly has been certified as acceptable. A similar approach can be used for wing spar or longeron inspection.

This measurement technique permits better identification of resonant modes because the standing wave effect on changes in amplitude based on transducer location is minimized. This, in turn, permits concentration on analysis of higher order amplitude signals from each crystal which will emphasis the influence of local structure or local resonance of a complex assembly. This, in turn, greatly simplifies the resonance spectrum and gives information by location on any deterioration of the component being measured.

What is claimed:

1. A method for resonant inspection for resonant maintenance comparison comprising the steps of:

measuring of resonant mode frequencies of at least one known good prototype part upon completion of manufacture of said known good prototype part to obtain known good part empirical resonant modal frequency data;

comparing resonant mode frequencies of at least one additional production part to the empirical resonant modal frequency data;

storing in an archival memory comparative data for each additional part by individual identity such as serial number; and inspecting said at least one additional production part at later production stages or maintenance intervals by comparing its resonant mode frequencies to said comparative archived data for that serial number.

2. The method in accordance with claim 1 further comprising the step of analyzing resonant frequency data for known good parts, to determine patterns accommodating the acceptable material and dimensional variations of parts that are deemed acceptable.

3. The method in accordance with claim 1, further comprising the steps of providing criteria for the identification of additional production parts that have unacceptable variations.

4. The method in accordance with claim 3 for then comprising the step of accepting or rejecting additional production parts based upon the criteria.

5. The method in accordance with claim 4 further comprising the step of accepting of said at least one additional production part for further nondestructive testing.

6. The method in accordance with claim 5 further comprising the steps of:

performing periodic maintenance and overhaul during which resonant ultrasound spectroscopy frequency (RUS) or equivalent comparison inspection is carried out on the production part; and comparing said overhaul resonant inspection measurements and pattern analysis to said stored individual serial number part archival resonant inspection comparative data to determine if there has been change in the part.

7. The method in accordance with claim 1 wherein the steps of measuring at least one production part resonant mode frequency include permanently attaching measurement transducers.

* * * * *